United States Patent
Thorley et al.

(10) Patent No.: US 7,500,967 B2
(45) Date of Patent: Mar. 10, 2009

(54) SINGLE USE SYRINGE

(75) Inventors: Craig S Thorley, Bolwarra (AU); Joseph H Kaal, Morpeth (AU)

(73) Assignee: Unitract Pty. Ltd., West Perth, Western Australia (AU)

( * ) Notice: Subject to any disclaimer, the term of this patent is extended or adjusted under 35 U.S.C. 154(b) by 451 days.

(21) Appl. No.: 10/258,385

(22) PCT Filed: Apr. 20, 2001

(86) PCT No.: PCT/AU01/00458

§ 371 (c)(1),
(2), (4) Date: Apr. 15, 2003

(87) PCT Pub. No.: WO01/80930

PCT Pub. Date: Nov. 1, 2001

(65) Prior Publication Data

US 2003/0158525 A1      Aug. 21, 2003

(30) Foreign Application Priority Data

Apr. 26, 2000   (AU) ................................. PQ7096
Jan. 18, 2001   (AU) ................................. PR2591

(51) Int. Cl.
*A61M 5/315*   (2006.01)
*A61M 5/00*    (2006.01)
(52) U.S. Cl. .................. 604/218; 604/110; 604/208
(58) Field of Classification Search .......... 604/240, 604/218, 110, 220, 208–10
See application file for complete search history.

(56) References Cited

U.S. PATENT DOCUMENTS

| | | | | |
|---|---|---|---|---|
| 4,978,339 A | * | 12/1990 | Labouze et al. ............ 604/110 |
| 5,346,480 A | * | 9/1994 | Hess et al. ................. 604/197 |
| 5,415,645 A | * | 5/1995 | Friend et al. ............... 604/110 |
| 5,533,970 A | * | 7/1996 | Berger et al. ............... 604/110 |
| 5,643,222 A | | 7/1997 | Mahurkar |
| 5,688,241 A | * | 11/1997 | Asbaghi ..................... 604/110 |
| 5,891,105 A | | 4/1999 | Mahurkar |
| 5,971,964 A | | 10/1999 | Donaldson |
| 6,033,386 A | | 3/2000 | Novacek et al. |
| 6,527,742 B1 | * | 3/2003 | Malenchek ................. 604/110 |
| 6,702,784 B1 | * | 3/2004 | Sheckler et al. ............ 604/181 |
| 6,926,697 B2 | * | 8/2005 | Malenchek ................. 604/197 |
| 7,001,364 B1 | * | 2/2006 | Farhi ......................... 604/198 |

FOREIGN PATENT DOCUMENTS

| | | |
|---|---|---|
| AU | 86142/98 | 4/1999 |
| DE | 38 33 138 | 4/1990 |
| DE | 3833138 A1 * | 4/1990 |
| EP | 0 339 954 | 11/1989 |
| EP | 0704225 A2 | 4/1996 |
| GB | 2266667 A | 11/1993 |
| RU | 2033194 C1 | 4/1995 |
| SU | 1759429 A1 | 9/1992 |

* cited by examiner

*Primary Examiner*—Kevin C. Sirmons
*Assistant Examiner*—Andrew M Gilbert
(74) *Attorney, Agent, or Firm*—Nixon Peabody LLP

(57) ABSTRACT

A single use retractable syringe and plunger are provided. The syringe has a barrel having a collar with one or two projections that slidably engage a plurality of interconnected slots of the plunger. The slots of the syringe include one or more gates or abutments that restrict slidable movement of the projections within the slots to thereby prevent re-use of the syringe after injection and subsequent retraction of the needle.

41 Claims, 14 Drawing Sheets

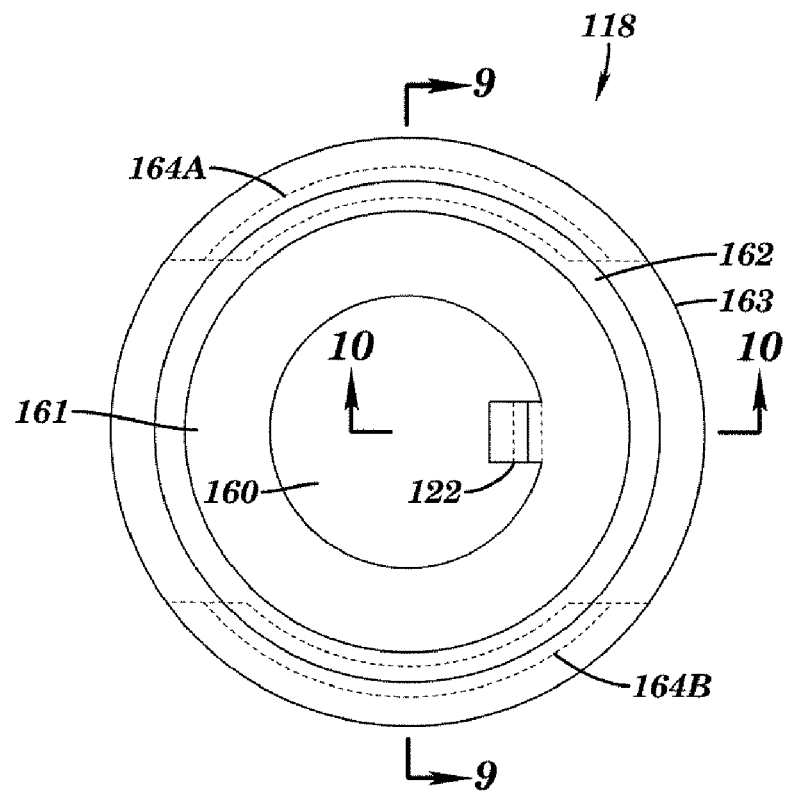
FIG. 8
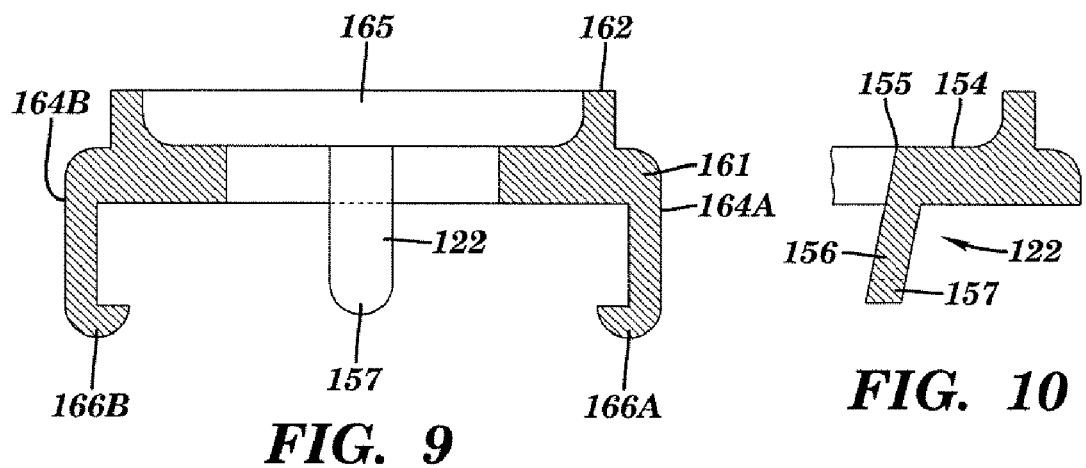
FIG. 9
FIG. 10

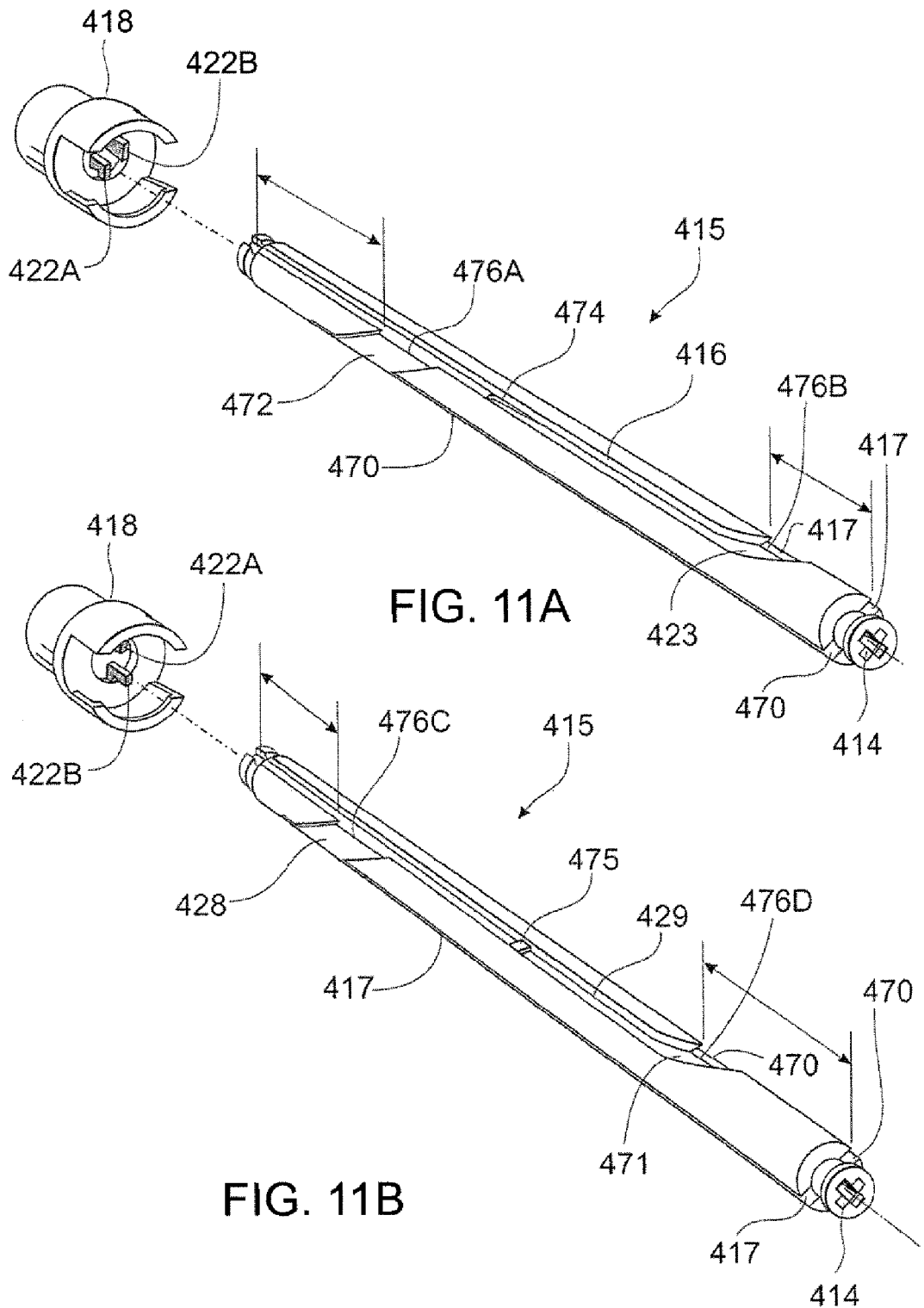

and Australian Application PQ7096, filed Apr. 26, 2000.

SINGLE USE SYRINGE

This application is a national stage application under 35 U.S.C. § 371 from PCT Application No. PCT/AU01/00458, filed Apr. 20, 2001, which claims benefit under 35 U.S.C. § 119 from Australian Application PR2591, filed Jan. 18, 2001, and Australian Application PQ7096, filed Apr. 26, 2000.

FIELD OF THE INVENTION

THIS INVENTION relates to syringes. In particular, this invention relates to a single use syringe and, more particularly, to a single use retractable syringe and plunger therefor.

BACKGROUND

The problems of shared syringes are notorious. The practice of sharing syringes without adequate sterilization between successive users is a major contributor to the transfer of Human Immunodeficiency Virus and Hepatitis with subsequent severe repercussions for the sufferer of such diseases and at a high cost to society of supporting and providing medical attention to those sufferers.

A lesser but still significant risk associated with unclean needles and syringes arises from the possibility of inadvertent needle-stick injuries. This is particularly a problem for law enforcement officers and paramedics who often encounter users of illegal drugs in their professional activities. Additionally, the habits of illegal drug users are such that dangerous byproducts of their activities, such as discarded syringes, are often left in places of public access presenting a risk to the users of areas such as public parks and school grounds.

There is clearly a need for an effective single use syringe which not only minimizes the chance of people sharing syringes, but also retracts a delivery needle into the syringe barrel, thereby inactivating the syringe and shielding the needle from inadvertent, harmful contact with other people.

Australian Patent Application No 86142198 (incorporated herein by reference in its entirety) to the present applicants discloses a single use syringe which goes a considerable way to addressing the above problem by providing a syringe barrel and plunger co-operating to rotate the plunger during use. When the plunger is rotated from its original orientation, a needle grasping mechanism is aligned with a receiving means in the needle seat. Once engaged by the grasping mechanism, the needle is retracted into the syringe barrel by retraction of the plunger.

However, the present inventors are aware that it is possible for an assiduous delinquent to re-use the above syringe by avoiding full depression of the plunger or by ensuring rotation of the plunger back into its original orientation during depression so that engagement of the plunger and needle does not occur.

SUMMARY OF THE INVENTION

In one aspect, the invention provides a plunger for a single use syringe having a co-operating barrel that has at least one projection, said plunger comprising a plurality of interconnected slots slidably engageable by said at least one projection, arranged so that slidable movement of said at least one projection within said slots is restricted to thereby prevent re-use of the syringe.

In another aspect, the invention provides a collar for a single use retractable syringe having a co-operating plunger that has at least two slots, said collar comprising first and second guiding projections slidably engageable with said at least two slots of said co-operating plunger.

In yet another aspect, the invention provides a single use retractable syringe having a plunger according to the aforementioned aspect.

Preferably, the plunger is for a single use syringe having a retractable needle that can be engaged by said plunger to facilitate retraction of the needle.

Preferably, the plunger comprises a movement restriction means that restricts slidable movement of said at least one projection within at least one of said plurality of slots.

Preferably, said movement restriction means may comprise one or more gates or abutments.

In one embodiment, the plunger is for a single use syringe having a co-operating barrel that has a single projection.

In this embodiment, said plurality of interconnected slots comprises a first slot and a second slot, said first slot deviating to meet said second slot.

Preferably, the plunger further comprises a gate that restricts movement of the projection from the second slot into the first slot.

Preferably, the plunger further comprises one or more gates or abutments in the second slot that upon engagement by said projection restrict withdrawal of the plunger.

Preferably, the plunger further comprises a retraction slot, connected by a deviation to the second slot, that facilitates retraction of the plunger.

In another embodiment, the plunger is for a single use syringe having a co-operating barrel that has first and second projections.

In this embodiment, said plurality of interconnected slots comprises a first slot, a second slot, a retraction slot and a fourth slot.

According to this embodiment, it is preferred that the retraction slot is connected by a deviation to said second slot, thereby facilitating complete retraction of said plunger.

Preferably, the first slot and the retraction slot each include an abutment engageable by said second projection and said first projection respectively, to prevent re-use of the syringe.

Preferably, the second slot includes a plurality of abutments engageable by said first projection to restrict withdrawal of the plunger.

Throughout this specification, unless otherwise indicated, "comprise", "comprises" and "comprising" are used inclusively rather than exclusively, so that a stated integer or group of integers may include one or more other non-stated integers or groups of integers.

BRIEF DESCRIPTION OF THE DRAWINGS

The present invention will now be described with reference to the embodiments disclosed in the accompanying drawings, wherein:

FIG. 8 is a top view of a collar for use with a syringe barrel;

FIG. 9 is a sectional view of the collar of FIG. 8 taken along the line 9-9;

FIG. 10 is a sectional view of a part of the collar of FIG. 8 taken along the line 10-10;

FIG. 11A is an exploded perspective view of one side of a plunger and collar;

FIG. 11B is an exploded perspective view of another side of the plunger and the collar shown in FIG. 11A;

DETAILED DESCRIPTION

Figure 1:
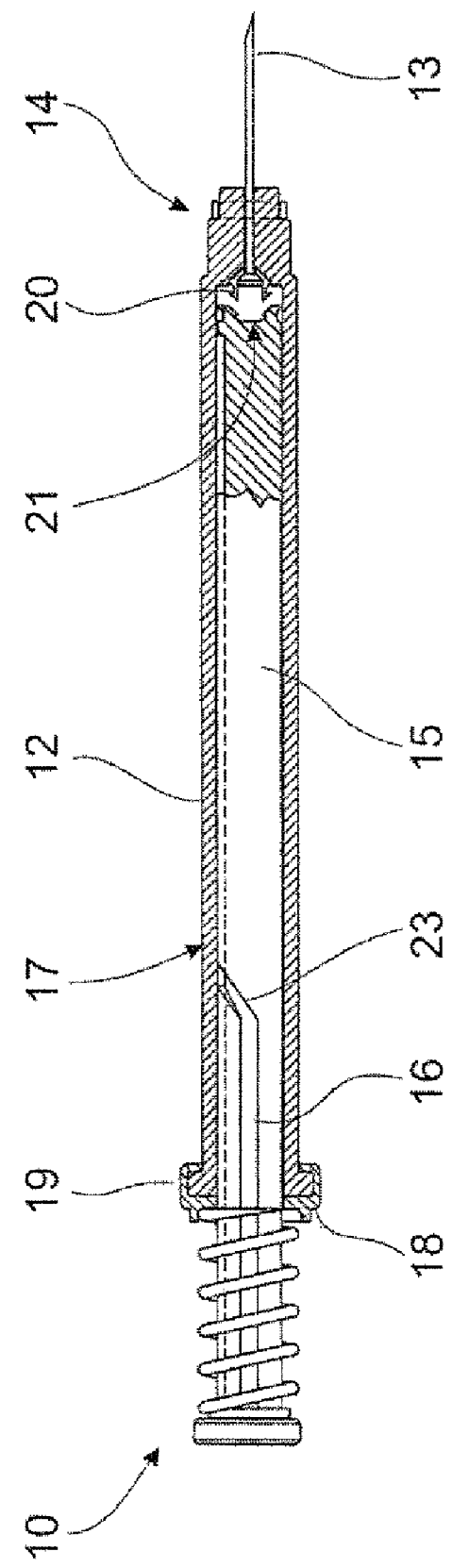
FIG. 1 is a schematic cross-sectional elevation view of retractable syringe disclosed in AU 86142/98.

In FIG. 1 there is shown a prior art retractable syringe 10, as disclosed in Australian Patent Application No 86142/98, which is incorporated herein by reference, syringe 10 comprising a hollow barrel 12, a needle 13 engaged with needle end 14 of plunger 15 that is slidably disposed in the hollow barrel 12. The plunger 15 is engageable with needle 13 so as to enable disengaging of needle 13 from barrel 12 as the plunger 15 is retracted following use. Retraction of the plunger 15 with which the needle 13 is engaged, draws the needle 13 into the hollow barrel 12, thus preventing accidental puncture of the skin with the used needle 13 or re-use by intravenous drug users.

In use, the plunger 15 is initially depressed towards the hollow barrel 12 needle end 14 to expel any air from the barrel 12. At the end of this initial depression, the plunger 15 does not engage the needle 13 so that the needle 13 remains engaged with barrel 12. Fluid to be injected is then drawn into the hollow barrel 12 through the needle 13 in the usual manner as the plunger is initially retracted.

To provide for the radial non-alignment of corresponding interlocking portions 20,21 on the initial depression of the plunger 15 to expel air, and for radial alignment on the subsequent depression of the plunger 15 to dispense fluid, a projection (not shown) sequentially engages first slot 16 and second slot 17 provided on the plunger 15. The projection is provided on collar 18 mounted onto the guiding end 19 of the barrel 12 during assembly of the syringe 10. The projection extends radially inwardly from collar 18 through which the plunger 15 slides. The collar 18 is fitted to barrel 12 such that the projection initially engages the first slot 16 prior to use, with engagement of the projection and first slot 16 radially non-aligning the corresponding interlocking portions 20, 21 such that they will not engage on initial depression of the plunger 15 to expel air from the hollow barrel 12.

The first slot 16 longitudinally extends from the guiding end 19 of plunger 15 to partway along the plungers length where the first slot 16 deviates circumferentially to meet the second slot 17. As a result of the deviation of the first slot 16 as plunger 15 is retracted to receive fluid into the hollow barrel 12 directly following its initial depression, the projection (not shown) on collar 18 will be guided from the first slot 16 through the deviation 23 and into the second slot 17. As the projection is fixed, this will result in the plunger being rotated through 90° so that the corresponding interlocking portions 21, 20 of the plunger 15 and needle 13, respectively align. The second slot 17 longitudinally extends along plunger 15 toward needle end 19. On the subsequent depression of the plunger 15 to dispense fluid, the corresponding interlocking portions 20, 21 will engage at the end of the stroke enabling disengagement of the needle 13 from barrel 12 and retraction of the needle 13 into barrel 12 as the plunger 15 is retracted.

Figure 2:
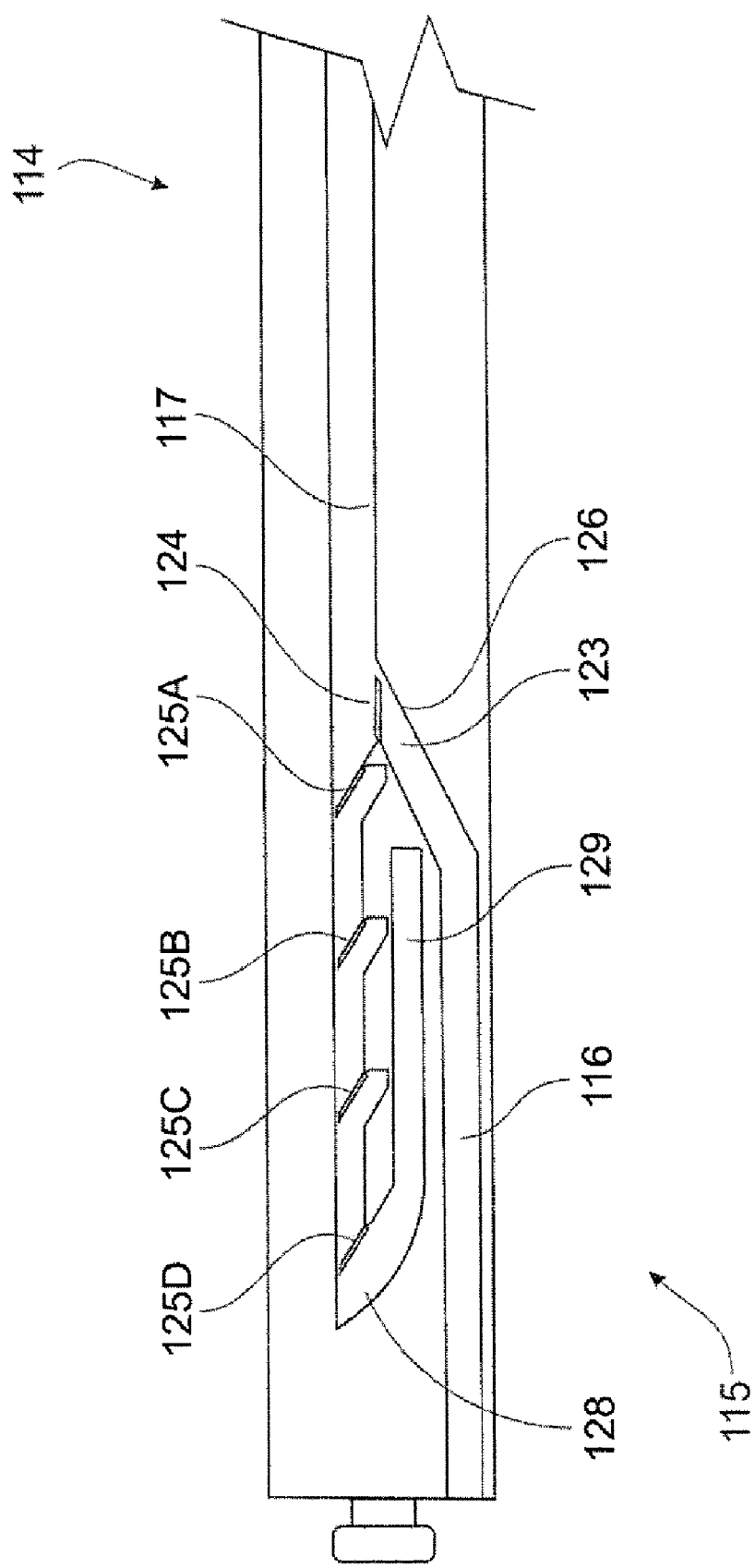
FIG. 2 is a side view of the plunger of the retractable syringe of a first embodiment of the present invention.
Figure 3:
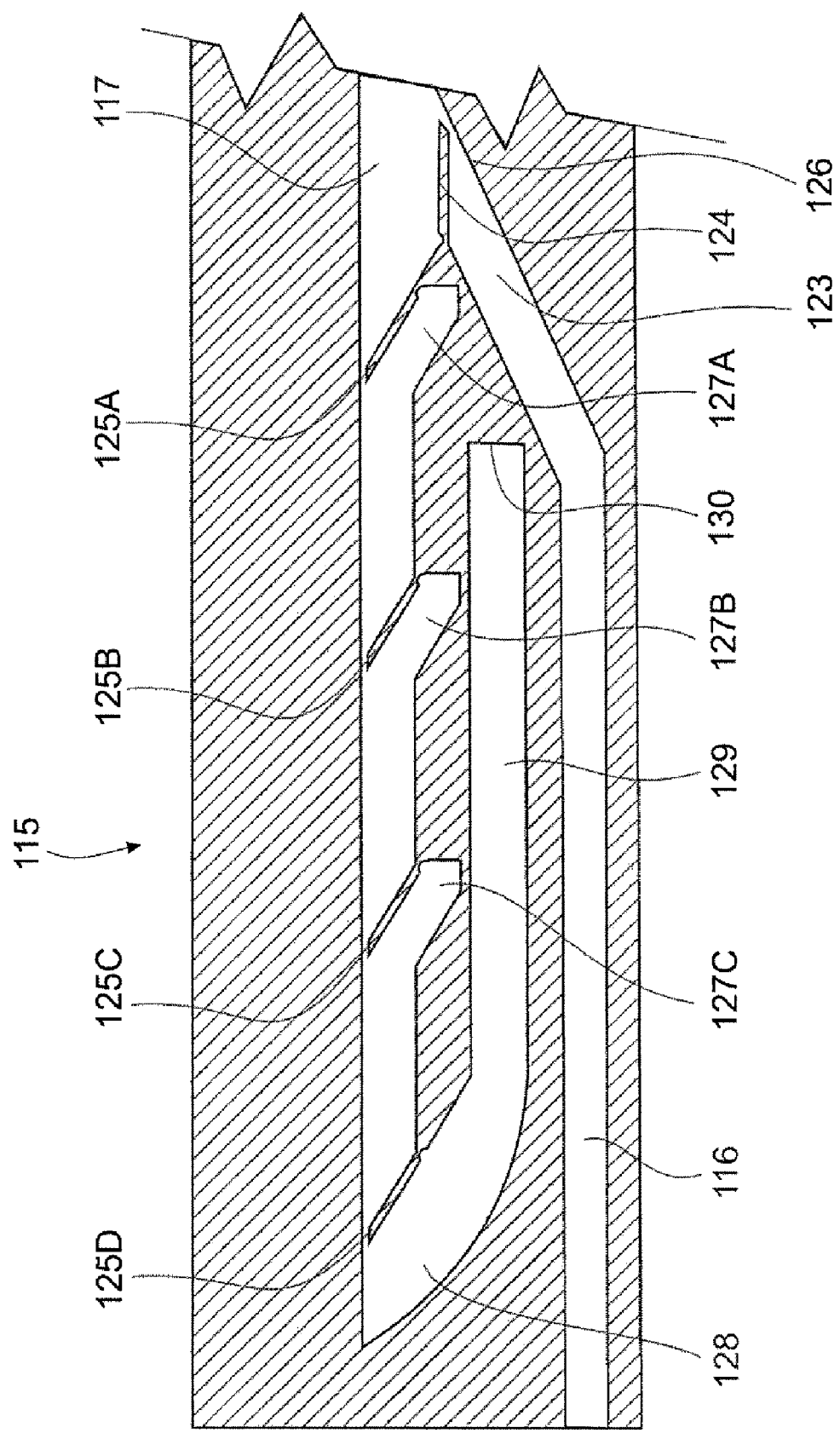
FIG. 3 is an enlarged view of the syringe plunger of FIG. 2.

An embodiment of a plunger 115 for a single use retractable syringe 110 according to the present invention is shown in FIG. 2 and FIG. 3. Collar 118 and projection 122 are best seen in FIGS. 7-10.

Referring to FIG. 2, first slot 116 second slot 117 are interconnected by first deviation 123. As noted previously in the prior art retractable syringe, it is possible for a drug abuser to redirect the plunger 115 during depression so that slot 116 is again engaged with the projection 122 so that full depression of the plunger 115 can occur without retraction of the needle.

To prevent this possibility, the inventors have inserted gate 124 at first deviation 123. The function of gate 124 is to allow passage of the projection 122 into slot 117 but to then prevent its re-entry into slot 116 after rotation of the plunger 115. After entry of the projection 122 into slot 117, plunger 115 will be permanently positioned so that corresponding interlocking portions on the plunger and needle (not shown in FIG. 2) are aligned.

The present inventors also note that it is possible for a syringe as disclosed in Australian Patent Application No 86142/98 to be used more than once if a user avoided full depression of plunger 115 in barrel 112. This restraint avoids engagement of the corresponding interlocking portions.

To create a means of preventing such use, the present inventors have provided gates 125A, 125B, 125C, 125D in second slot 117. These gates are offset in a direction that allows projection 122 on collar 118 to pass along slot 117 and through the gates 125A-D towards the end of the plunger 115 distal to needle end 114. That is, the gates 125A-D allow depression of the plunger 115. However, whenever the projection 122 passes through gate 125, it is blocked from re-entry into the portion of the slot 117 that it just exited by abutting one of gates 125A, B, C or D. That is, withdrawal of the plunger in the barrel is prevented by gates 125A-D.

However, as the plunger 115 is depressed and the interlocking portions (not shown) are aligned, the plunger 115 engages the needle for retraction. The plunger 115, however, cannot be withdrawn along slot 117 because of the presence of the gates 125A-D against which projection 122 abuts. A retraction slot 129 is therefore provided to allow retraction of the plunger 115 when engaged with the needle of the syringe. Retraction slot 129 and second slot 117 are interconnected by second deviation 128.

Referring now to FIG. 3, sliding movement of projection 122 from first slot 116 to second 117 is straightforward. However, any attempt to slidably move the projection 122 back into first slot 116 will encounter gate 124. Any attempt to force gate 124 will lead to its jamming against the wall 126 of deviation 123. Any subsequent additional force applied is unlikely to be successful in forcing the projection 122 back into slot 116. Even if the integrity of gate 124 is destroyed, it is likely the deformed gate will jam, thereby preventing further use of the syringe 110. Gates 125A-D operate on a similar principle. However, gates 125A, B and C are situated adjacent respective recesses 127A, B and C in the substantive structure of the plunger 115. These recesses provide a nesting position for projection 122. Recesses 127 A-C also provide clearance for adjacent gates 125 during passage of projection 122 so that the gates 125 clear slot 117. For example, gate 125B does not obstruct the passage of projection 122 when forced into recess 127C.

As shown in FIG. 2 and FIG. 3, gate 125D adjoins second deviation 128 into retraction slot 129. Retraction slot 129 allows retraction of the plunger 115 (and an engaged needle) once fully depressed after projection 122 has proceeded through gate 125D and second deviation 128. Second deviation 128 between second slot 117 and retraction slot 129 is circumferential and movement of projection 122 therethrough drives further 90° rotation of the plunger 115. At this point, the needle is positively engaged with the plunger 115. The needle 113 may then be safely retracted into the barrel 112 of the syringe 110 by retraction of plunger 115 until the projection 122 encounters terminal wall 130 of retraction slot 129.

Figure 4:
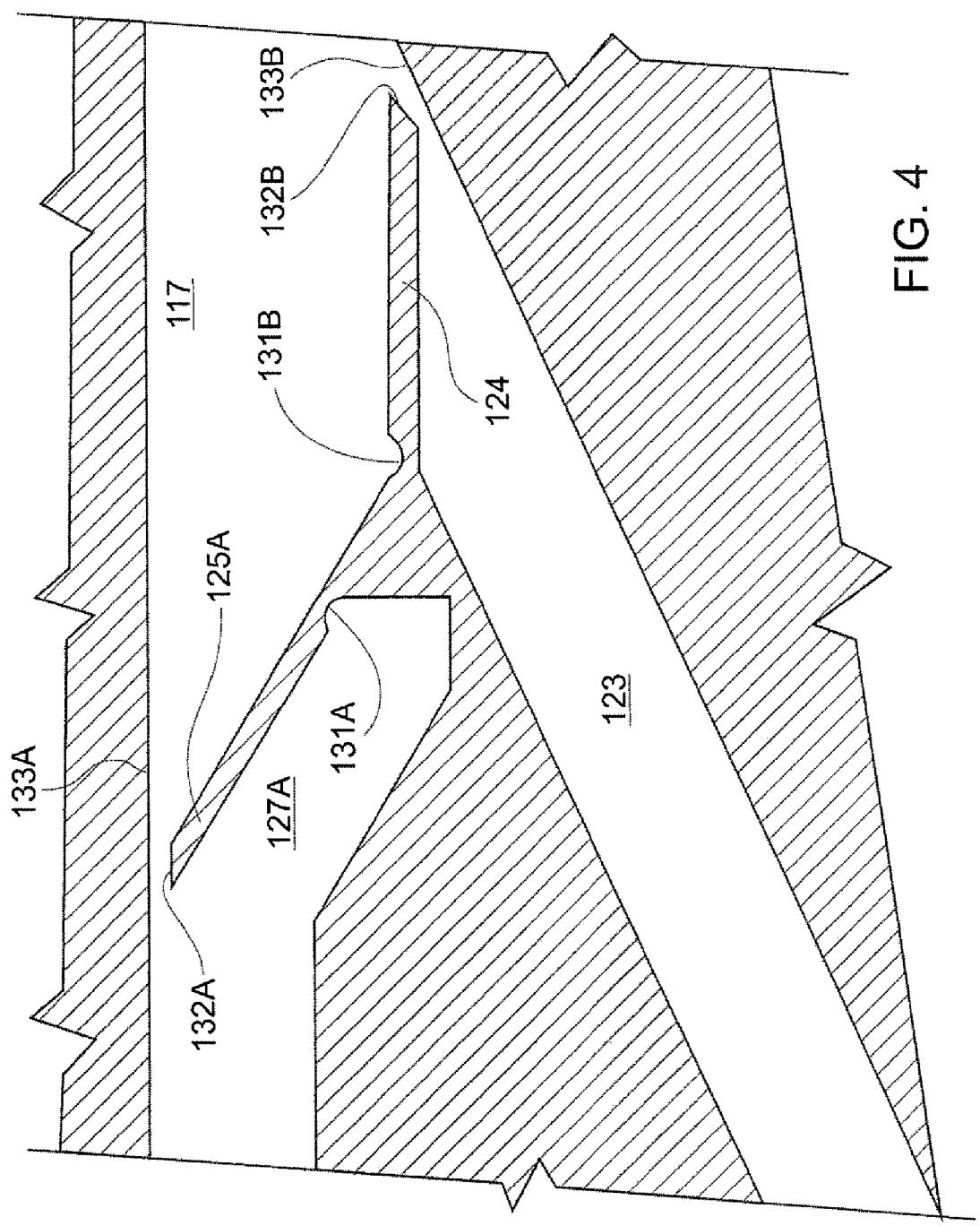
FIG. 4 is a detailed view of the junction between a first and second slot in the syringe plunger of FIG. 2.
Figure 5:
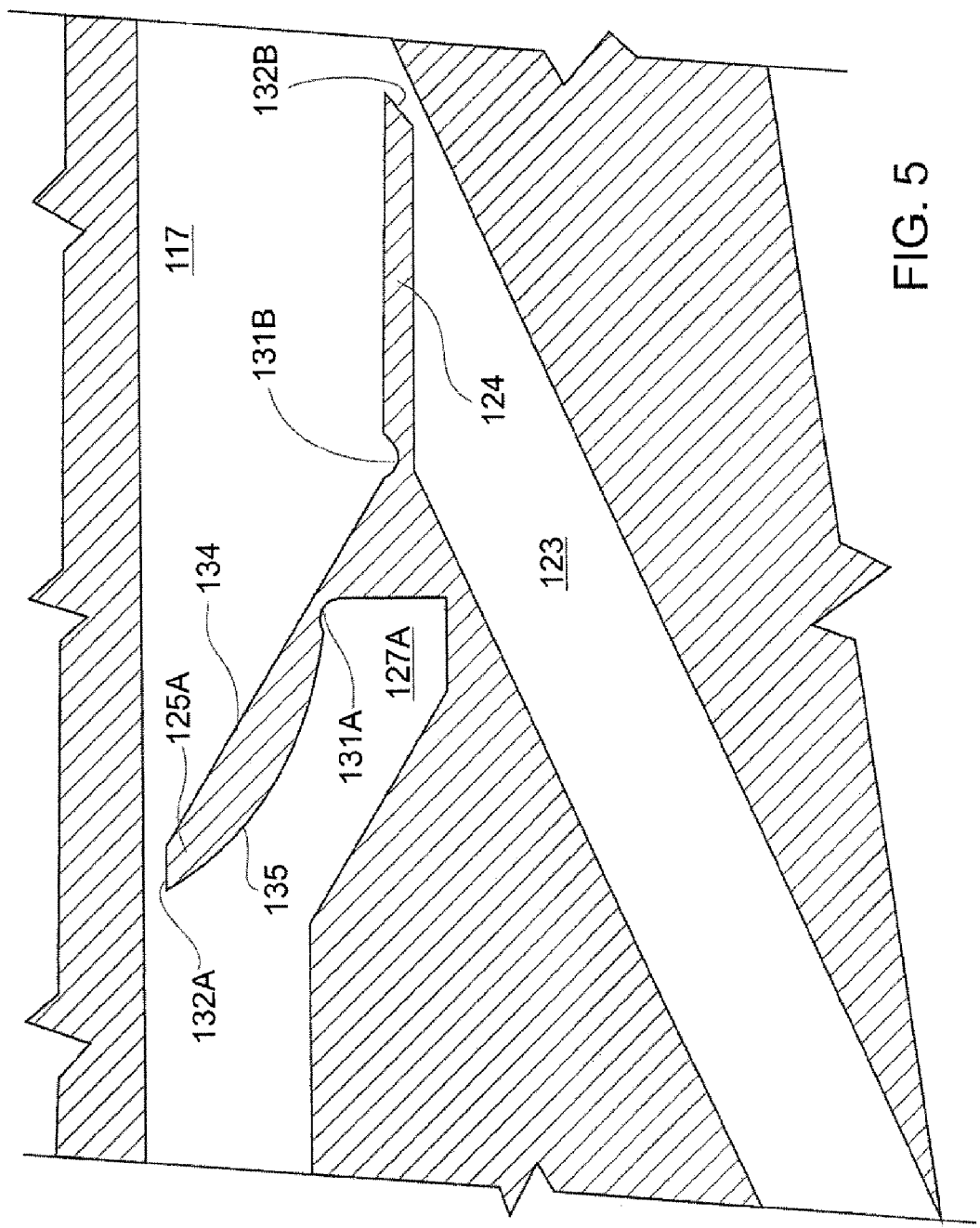
FIG. 5 is a detailed view of the junction of a first and second slot in a further embodiment of a syringe plunger of the invention.

In FIGS. 4 and 5, there are shown various configurations of gate 124 and gates 125A-D. In FIG. 4, scalloped undercut 131A is present in gate 125A, and scalloped undercut 131B is present in gate 124. These undercuts provide respective soft hinges to facilitate easy operation of the plunger 115. This view also shows the outer edges 132A and 132B of offset gate 125A and gate 124 respectively, which are substantially parallel to adjoining surfaces 133A and 133B respectively. This increases the area of contact should any attempt be made to force the guiding projection in an undesired direction.

Referring to FIG. 5, gate 125A has a front face 134 and rear face 135. Rear face 135 describes an arc which gives an increased thickness to the gate 125A and thereby increases its strength. This also provides a smooth curved entry into recess 127A for projection 122 should retraction be attempted after the projection 122 has passed gate 125A. It is again clear in this view that gate 125A will hingedly move into recess 127A during passage of projection 122.

Figure 6:
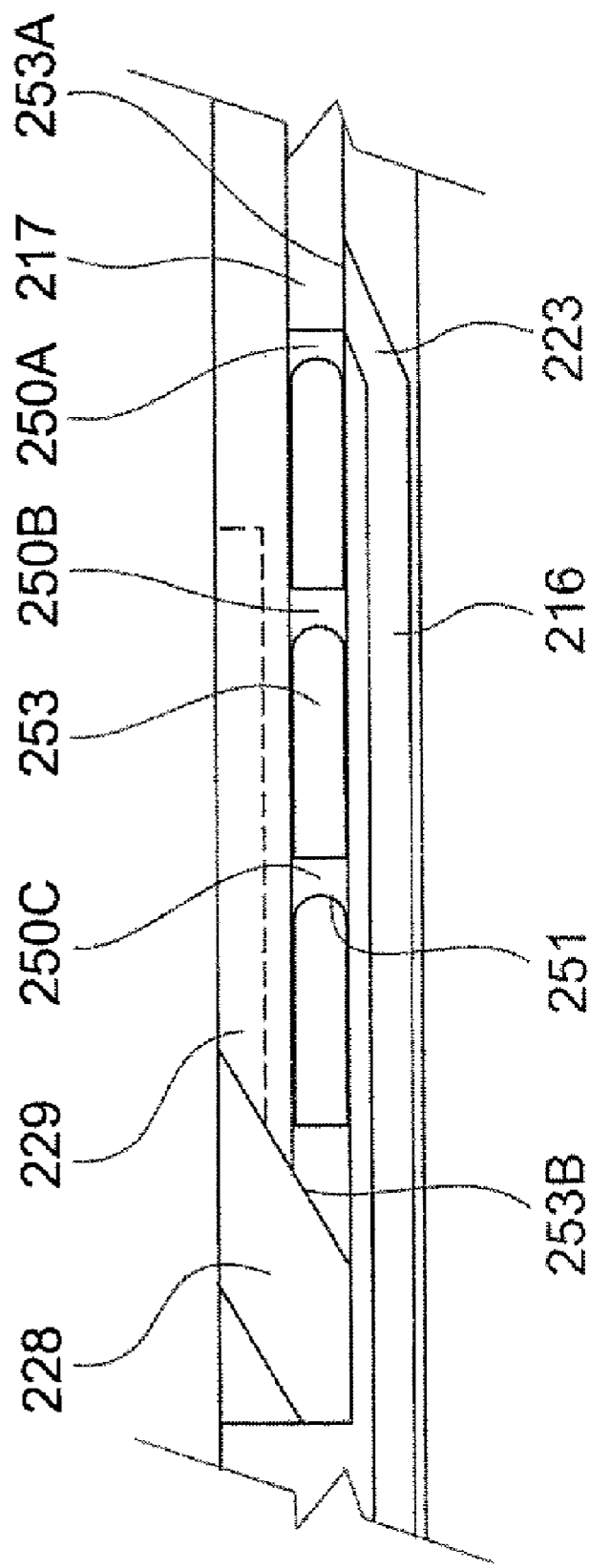
FIG. 6 is a top view of a still further embodiment of a plunger of the invention.
Figure 7A:
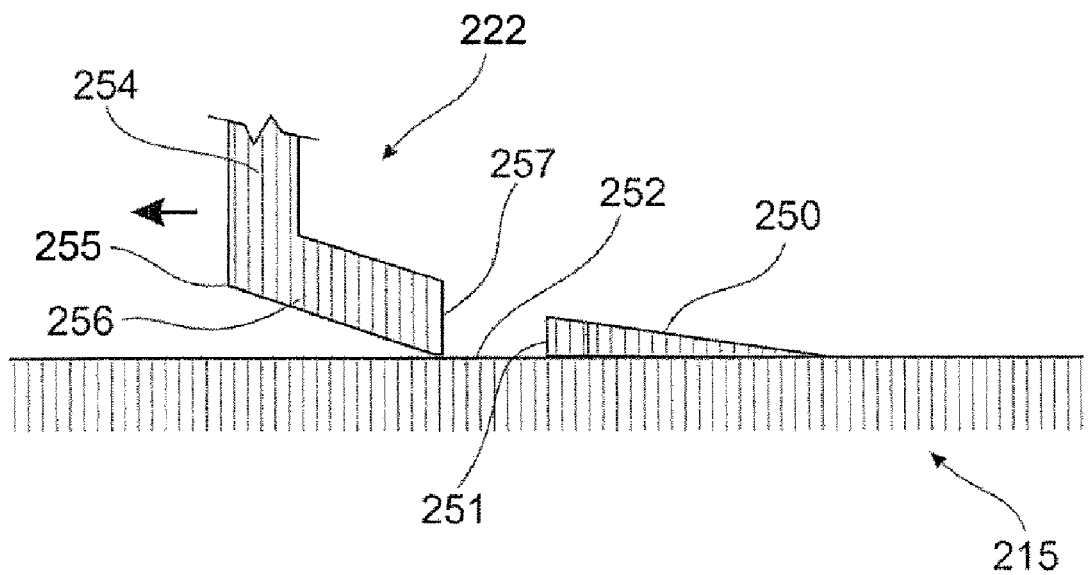
FIG. 7A is a side view of a portion of the plunger of FIG. 6 and a corresponding guiding projection of a syringe barrel wherein a second slot of the plunger comprises a single abutment in the form of a ramp.
Figure 7B:
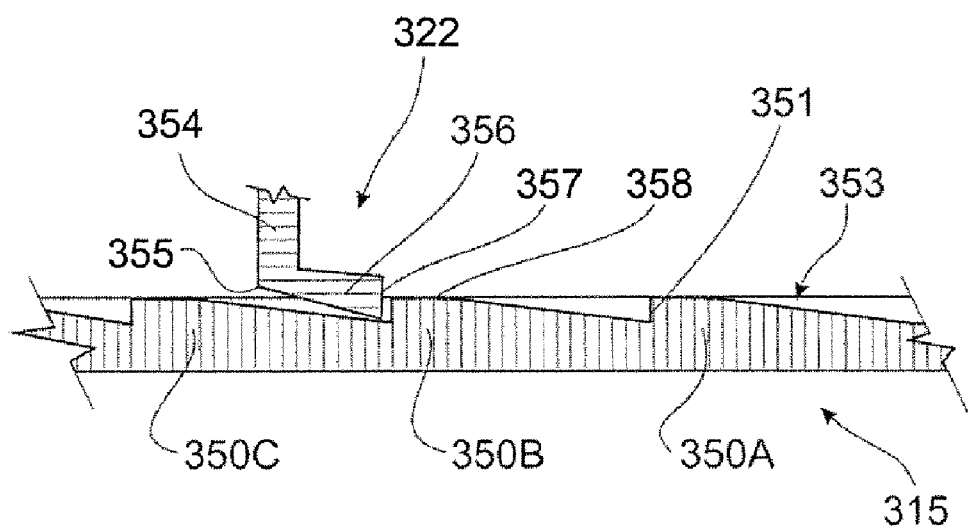
FIG. 7B is a side view of another portion of the plunger of FIG. 6 and a corresponding guiding projection of a syringe barrel wherein a second slot of the plunger comprises a plurality of ramps.
Figure 11C:
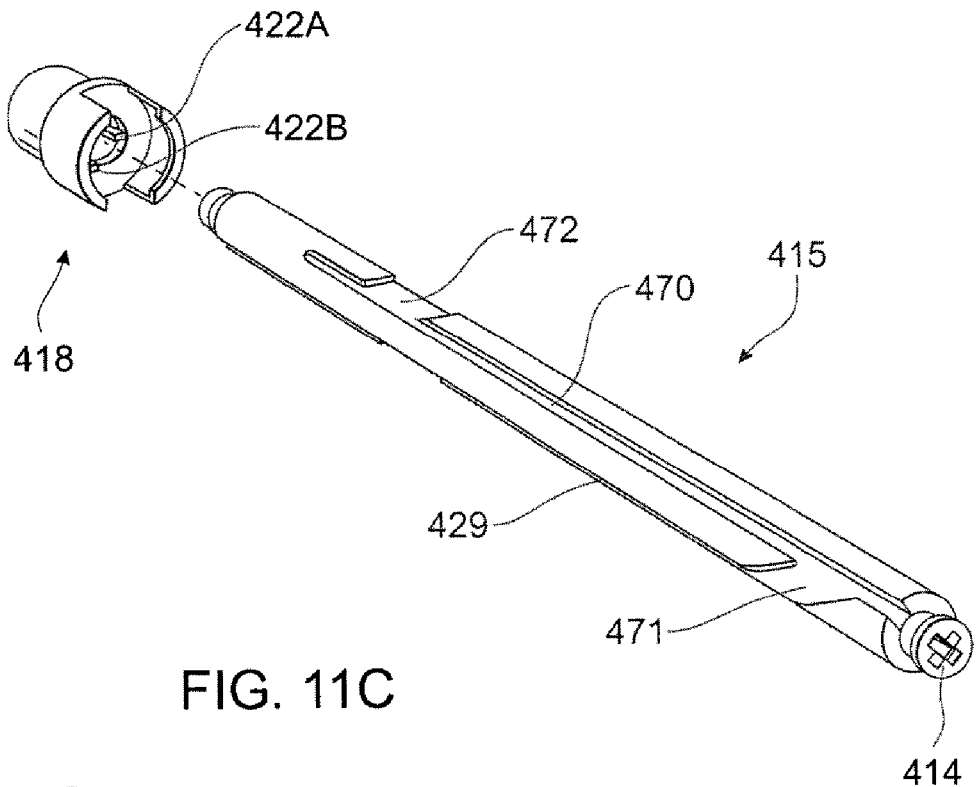
FIG. 11C is another exploded perspective view of the plunger and collar shown in FIG. 11A.
Figure 11D:
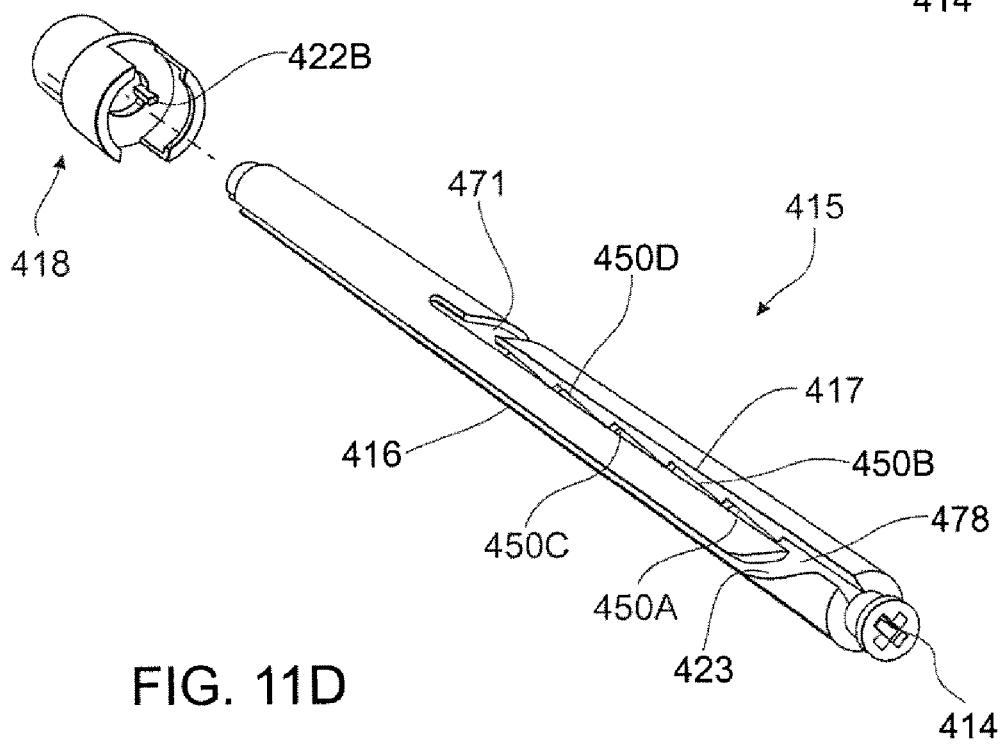
FIG. 11D is yet another exploded perspective view of the plunger and the collar shown in FIG. 11A.

In FIGS. 6, 7A, and 7B there are shown other means by which retraction of plunger 115 may be restricted or prevented when projection 122 engages second slot 117.

FIG. 6 is a part view of an embodiment of plunger 215 of the invention in which offset gates 225A-D in slot 217 are replaced by a series of abutments such as ramps 250A-C. Each ramp 250 terminates in curved face 251 rising from the base 252 of second slot 217. Also present are ledges 253A and 253B located at the junction of deviation 223 and second slot 217 and at the junction of second slot 217 and second deviation 228 respectively.

It is noted that during initial retraction, projection 222 slidably moves from first slot 216 into first deviation 223 and then across ledge 253A into second slot 217. Projection 222 is thereby restrained from re-entry into first deviation 223 by abutting against ledge 253A. Furthermore, projection 222 slidably moves from second slot 217 across ledge 253B into second deviation 228. Projection 222 is thereby restrained from re-entry into second slot 217 by abutting against ledge 253B.

FIG. 7A is a side sectional view of a ramp 250 of the embodiment of FIG. 6, wherein projection 222 is in the form of an arm having a proximal member 254, an elbow 255 and a distal member 256. Distal member 256 terminates in a curved surface 257 which is complementary to curved face 251 of ramp 250. In operation, guiding projection 222 is resilient and slides along base 252. As the plunger 215 is retracted in the direction indicated by the arrow, projection 222 is displaced by the ramp 250. The projection 222 is tensioned as it is slid up the ramp 250. Projection 222 then flicks or snaps into engagement with base 252 of slot 217 once it has cleared the ramp 250. Engagement between complementary curved face 251 of ramp 250 and curved surface 257 of projection 222 prevents, or at least makes more difficult, any attempt to depress the plunger 215 subsequent to its withdrawal after use.

It will be appreciated by the skilled person that the number of ramps 250 or offset gates 125 present may be varied as desired and that the number described herein is merely for the purposes of illustration. FIG. 7B shows multiple ramped abutments 350A, B and C each having a respective plateau 358, in contrast to the continuously-sloped ramp 250 shown in FIG. 7A.

FIG. 8 shows a top view of collar 118 suitable for use with a syringe barrel in the present invention. Although the collar 118 is described as separate from the barrel, it is understood that reference to a barrel in this specification will, where appropriate, include reference to a barrel and collar. While it is possible to mount the projection on the barrel itself, it is more efficient and practical to do so on collar 118 for use with the syringe.

Collar 118 has a central aperture 160 for location of a plunger 115 according to the present invention. The collar 118 also has a body 161 and an upper circular wall 162 which defines a seat 165 for receiving plunger 115. The collar 118 has an outer wall 163 which is continuous with barrel-engaging arms 164A, 164B seen in hidden detail. Projection 122 extends into the aperture 160.

FIG. 9 is a sectional view taken along the line 9-9 and shows the projection 122 with curved end 157. Wall 162 defines seat 165 for receiving an end of a syringe plunger. The body 161 is continuous with the barrel-grasping arms 164A and 164B which respectively terminate in hooks 166A and 166B.

FIG. 10 is a sectional view of a part of the cap of FIG. 8 taken along the line 10-10. This view shows projection 122 formed by proximal portion 154, elbow 155 and distal portion 156 terminating in curved end 157. The elbow forms an angle of slightly greater than 90° that the projection slopes towards the surface of a co-operating plunger (not seen). Preferably, projection 122 is resiliently flexible so that displacement of the end 157 when engaging a ramp 150, for example, will be followed by a flick back once the projection 122 clears the ramp 150. The distal portion 156 will be displaced radially outwardly by such a ramp followed by a radially inwards snap rebound on passage of ramp 150.

The radius on the end of projection 122 helps turn the plunger 115 relative to the barrel 112 when it travels from the first slot 116 to the second slot 117 or, alternatively, from the second slot 117 to the retraction slot 129.

Another advantage of the curved end 157 of projection 122 is that it only has point contact on ramp 150 as it moves across the ramp. Clearly, it is necessary that any flexion of the projection will be retained in the slot in which it is located as any protrusion beyond that slot would foul movement of the plunger relative to the wall of a surrounding barrel.

Another embodiment of the present invention is shown in FIGS. 11-15.

In FIGS. 11A-11D and 12, it can be seen that plunger 415 has first slot 416 interconnected to second slot 417 via first deviation 423, second slot 417 interconnected to retraction slot 429 via second deviation 428, retraction slot 429 interconnected to fourth slot 470 via third deviation 472 and fourth slot 470 interconnected to first slot 416 via fourth deviation 471. First slot 416 and retraction slot 429 are longitudinally offset with respect to each other; second slot 417 and fourth slot 470 are longitudinally offset with respect to each other; first deviation 423 and third deviation 471 are longitudinally offset with respect to each other; and second deviation 428 and fourth deviation 472 are longitudinally offset with respect to each other; as indicated by arrows in FIGS. 11A-11B.

Figure 12:
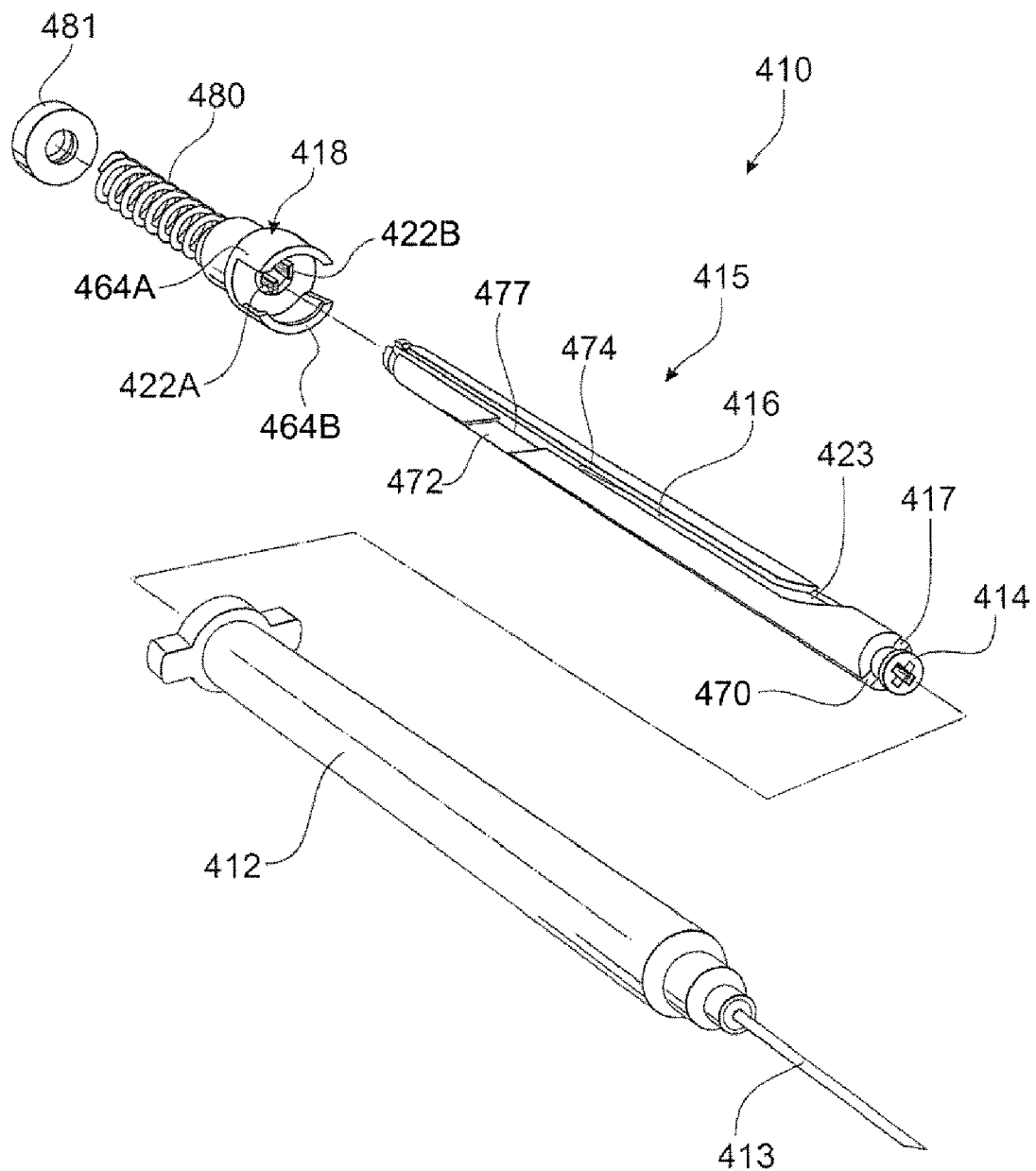
FIG. 12 is an exploded perspective view of a retractable single use syringe.
Figure 13:
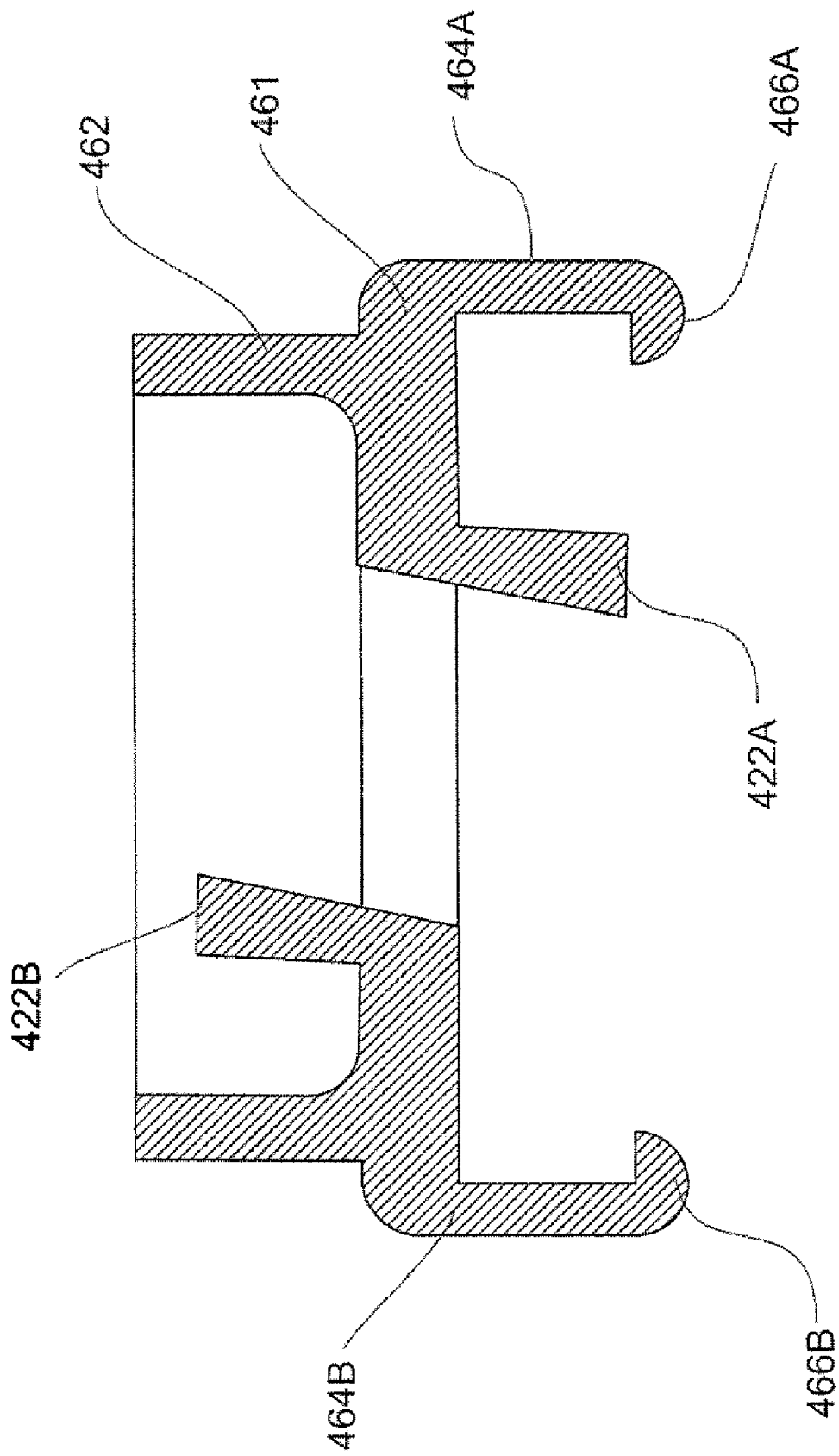
FIG. 13 is a sectional view of a collar having first and second guiding projections.

Referring to FIG. 12 and FIG. 13 in particular, collar 418 has body 462, barrel-engaging arms 464A and 464B, first projection 422A and second projection 422B which are longitudinally offset with respect to each other. Furthermore, first projection 422A projects in a direction opposite to that of second projection 422B when assembled into syringe 410, that is toward needle end 414.

Figure 14A:
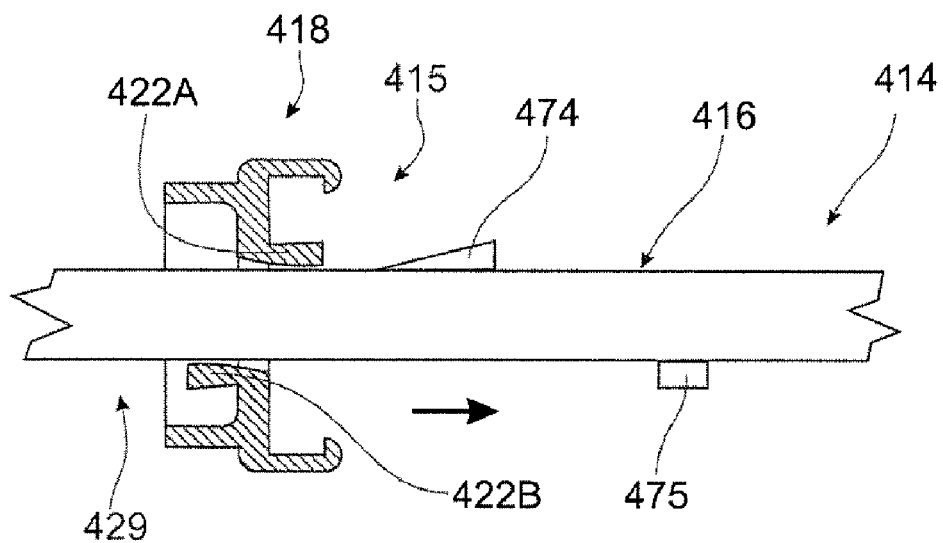
FIG. 14A is a sectional elevation view of a plunger and collar having first and second projections during initial depression of the plunger to expel air from the barrel.

Referring now to FIG. 14A, initially in use, first projection 422A is located in first slot 416 and second projection 422B is located in retraction slot 429, maintained in this position by spring 480 which bears against cap 481 (in use mounted to plunger 415) and collar 418. First slot 416 includes an abutment in the form of ramp 474. This ramp 474 does not restrict slidable movement of projection 422A in first slot 416. An abutment 475 is also located in retraction slot 429. Abutment 475 in retraction slot 429 is block-shaped, although abutment 475 may be in the form of a ramp. Limited slidable movement of second projection 422B (relative to plunger 415) is allowed in the direction of the arrow in FIG. 14A, such as when initially depressing plunger 415 to expel air from barrel 412.

Figure 14B:
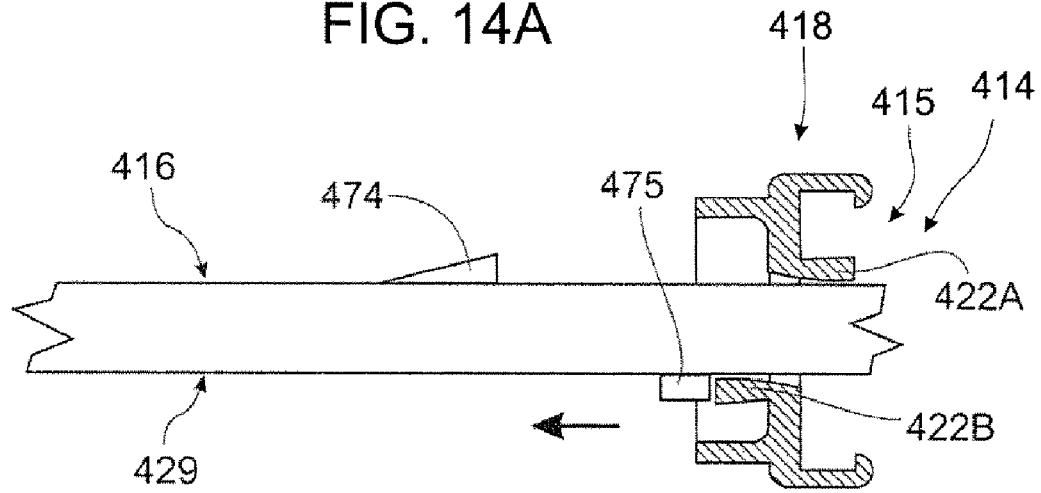
FIG. 14B is a sectional elevation view of the plunger and collar after initial withdrawal of the plunger to fill the syringe barrel.

Referring now to FIG. 14B, withdrawal of plunger 415 occurs to a point where projections 422A and 422B move over and beyond abutment 474 and abutment 475 respectively. As previously described, projections 422A and 422B are preferably resiliently flexible and are therefore tensioned as they pass over ramp 474 and abutment 475 respectively. Projections 422A and 422B then snap back into engagement with slots 416 and 429 respectively. Because projection 422B faces guiding end 419 of barrel 412, plunger 415 is prevented from slidable movement back in the direction from which it came by second projection 422B bearing against abutment 475. This restricts depression of plunger 415 so that any material in the barrel cannot be expelled. Thus, completion of plunger 415 withdrawal in the direction of the arrow in FIG. 14B must be performed or else material in the syringe barrel cannot be injected.

It should be noted that because projections 422A and 422B are longitudinally offset, as are fourth deviation 472 and second deviation 428, in use projections 422A and 422B are guided along first slot 417 and retraction slot 429 respectively, unable to be rotated back into fourth slot 470 and second slot 417 respectively. It is also noted that abutments in the form of ledges 476A, 476B, 476C and 476D are provided that assist in guiding the projections 422A and/or 422B into appropriate slots. These prevent undesirable movement of projection 422A or 422B back into the deviation from whence they exited by virtue of projection 422A and/or 422B bearing against the ledge located at the junction of each respective deviation and slot.

Completion of plunger withdrawal is followed by first projection 422A slidably moving into second slot 417 via first deviation 423 and second projection 422B slidably moving from retraction slot 429 into fourth slot 470 via deviation 471. This causes a 90° C. rotation of plunger 415 with respect to collar 418 and barrel 412.

Depression of plunger 415 to inject material in barrel 415 occurs when first projection 422A is slidably located in second slot 417 and second projection 422B is slidably located in fourth slot 470.

Figure 15:
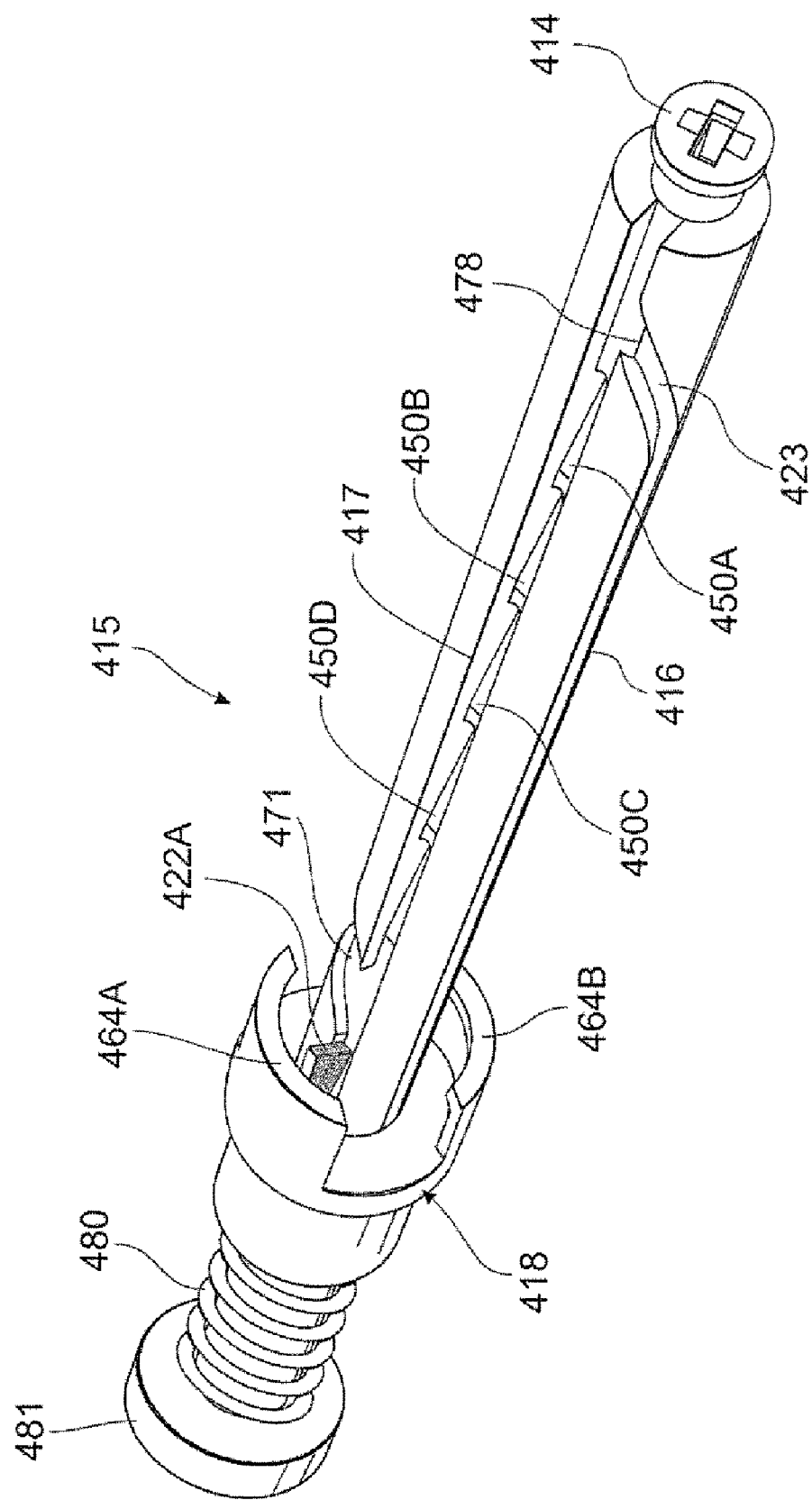
FIG. 15 is a perspective view of a plunger and collar showing a plurality of abutments in a second slot of the plunger.

As best seen in FIG. 15, second slot 417 has a plurality of abutments, in this case in the form of ramps 450A, 450B, 450C and 450D. As plunger 415 is depressed to inject, first projection 422A bears against any respective one of ramps 450A, 450B, 450C and 450D to restrict retraction of plunger 415, in a similar fashion to that described in previous embodiments. Second projection 422B, however, is freely slidable within fourth slot 470.

At the end or depression of plunger 415, needle end 414 of plunger 415 is aligned with and engages needle 413 as hereinbefore described.

During retraction of needle 413, first projection 422A is moved into retraction slot 429 via second deviation 428, while second projection 422B moves from fourth slot 470 into first slot 416 via fourth deviation 472. This results in a further 90° rotation of plunger 415 with respect to collar 418 and barrel 412. At the completion of retraction of needle 413 into the position shown in FIG. 14C, plunger 415 has rotated a total of 180°.

Figure 14C:
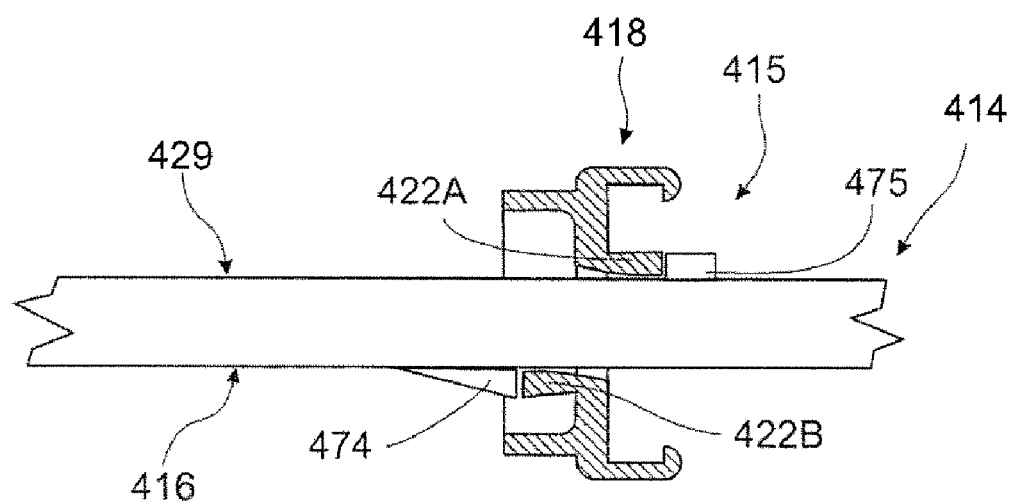
FIG. 14C is a sectional elevation view of the plunger and collar after needle retraction.

As shown in FIG. 14C, following retraction of plunger 415 and needle 413, second projection 422B comes to bear against abutment 474 in first slot 416 thereby preventing depression of plunger 415; first projection 422A comes to bear against abutment 475 in retraction slot 429 thereby preventing withdrawal or retraction of plunger 415, thus rendering the syringe 410 inoperable beyond first use.

Throughout the specification, the aim has been to describe the preferred embodiments of the invention without limiting the invention to any one embodiment or specific collection of features. Various changes and modifications may be made to the embodiments described and illustrated without departing from the present invention. In particular, it is contemplated that gates, abutments, ledges and other means disclosed herein for restricting plunger movement may be readily interchanged as desired by the skilled person.

The invention claimed is:

1. A plunger for a single use syringe having a co-operating barrel and a retractable needle engaged therewith, said plunger engageable with said retractable needle to facilitate retraction of said needle into said barrel, wherein said barrel has at least first and second projections and said plunger has a plurality of interconnected slots comprising a first slot, a second slot, a retraction slot and a fourth slot, said first slot connected to said second slot by a first deviation, said second slot connected to said retraction slot by a second deviation, said retraction slot connected to said fourth slot by a third deviation and said fourth slot connected to said first slot by a fourth deviation, which slots are slidably engageable by the first and second projections, whereby initially said first projection is locatable in said first slot and is capable of slidably moving from said first slot through said first deviation into said second slot and subsequently from said second slot through said second deviation into said retraction slot; and initially said second protection is locatable in said retraction slot and is capable of slidably moving from said retraction slot through said third deviation into said fourth slot and subsequently from said fourth slot through said fourth deviation into said first slot; wherein said slots are arranged so that slidable movement of said respective projections within said slots is restricted to thereby prevent re-use of the syringe.

2. The plunger of claim 1, wherein the second slot includes a plurality of abutments engageable by said first projection to restrict withdrawal of said plunger.

3. The plunger of claim 1, wherein the first slot includes an abutment engageable by said second projection to restrict depression of said plunger.

4. The plunger of claim 1, wherein the retraction slot includes an abutment engageable by said first projection to restrict withdrawal of said plunger after retraction is complete.

5. The plunger of claim 1, wherein said retraction slot includes an abutment engageable by said second projection to restrict depression of said plunger.

6. A single use retractable syringe comprising:
a barrel;
a retractable needle; and
a plunger engageable with said retractable needle to facilitate retraction of the needle into the barrel, wherein the barrel has at least first and second projections and the plunger has a plurality of interconnected slots comprising a first slot, a second slot, a retraction slot and a fourth slot, said first slot connected to said second slot by a first deviation, said second slot connected to said retraction slot by a second deviation, said retraction slot connected to said fourth slot by a third deviation and said fourth slot connected to said first slot by a fourth deviation, which slots are slidably engageable by the first and second projections, whereby initially said first projection is locatable in said first slot and is capable of slidably moving from said first slot through said first deviation into said second slot and subsequently from said second slot through said second deviation into said retraction slot; and initially said second projection is locatable in said retraction slot and is capable of slidably moving from said retraction slot through said third deviation into said fourth slot and subsequently from said fourth slot through said fourth deviation into said first slot; wherein said slots are arranged so that slidable movement of said respective projections within said slots is restricted to thereby prevent re-use of the syringe.

7. The syringe of claim 6, wherein the second slot includes a plurality of abutments engageable by the first projection to restrict withdrawal of the plunger.

8. The syringe of claim 6, wherein the first slot includes an abutment engageable by the second projection to restrict depression of the plunger.

9. The syringe of claim 6, wherein the retraction slot includes an abutment engageable by the first projection to restrict withdrawal of the plunger after retraction is complete.

10. The syringe of claim 6, wherein the retraction slot includes an abutment engageable by the second projection to restrict depression of the plunger.

11. A method for making a single use retractable syringe, the method comprising:
providing a barrel with a retractable needle adjacent one end of the barrel; and
slidably disposing at least a portion of a plunger in another end of the barrel, the plunger engageable with the retractable needle to facilitate retraction of the needle into the barrel, wherein the barrel has at least first and second projections and the plunger has a plurality of interconnected slots comprising a first slot, a second slot, a retraction slot and a fourth slot, said first slot connected to said second slot by a first deviation, said second slot connected to said retraction slot by a second deviation, said retraction slot connected to said fourth slot by a third deviation and said fourth slot connected to said first slot by a fourth deviation, which slots are slidably engageable by the first and second projections, whereby initially said first projection is locatable in said first slot and is capable of slidably moving from said first slot through said first deviation into said second slot and subsequently from said second slot through said second deviation into said retraction slot; and initially said second projection is locatable in said retraction slot and is capable of slidably moving from said retraction slot through said third deviation into said fourth slot and subsequently from said fourth slot through said fourth deviation into said first slot; wherein said slots have a movement restriction system so that slidable movement of the projections within the slots is restricted to a first path to prevent re-use of the syringe.

12. The method of claim 11, wherein the second slot includes a plurality of abutments engageable by the first projection to restrict withdrawal of the plunger.

13. The method of claim 11, wherein the first slot includes an abutment engageable by the second projection to restrict depression of the plunger.

14. The method of claim 11, wherein the retraction slot includes an abutment engageable by the first projection to restrict withdrawal of the plunger after retraction is complete.

15. The method of claim 11, wherein the retraction slot includes an abutment engageable by the second projection to restrict depression of the plunger.

16. The plunger of claim 2 further comprising at least one recess adjacent at least one of the abutments, the at least one recess is sized to provide a nesting position for at least one of the first and second projections.

17. The plunger of claim 2 further comprising at least one undercut region in at least one of the abutments.

18. The plunger as set forth in claim 2 wherein an outer edge on at least one of the abutments is substantially parallel to an opposing surface on the one of the barrel and plunger with the plurality of interconnected slots.

19. The plunger as set forth in claim 2 wherein a rear face on at least one of the abutments has an arc shape.

20. The plunger as set forth in claim 1 wherein the first and second projections extend in at least partially opposing directions.

21. The syringe of claim 7 further comprising at least one recess adjacent at least one of the abutments, the at least one recess is sized to provide a nesting position for at least one of the first and second projections.

22. The syringe of claim 7 further comprising at least one undercut region in at least one of the abutments.

23. The syringe as set forth in claim 7 wherein an outer edge on at least one of the abutments is substantially parallel to an opposing surface on the one of the barrel and plunger with the plurality of interconnected slots.

24. The syringe as set forth in claim 7 wherein a rear face on at least one of the abutments has an arc shape.

25. The syringe as set forth in claim 6 wherein the first and second projections extend in at least partially opposing directions.

26. The method of claim 12 further comprising forming at least one recess adjacent at least one of the abutments, the at least one recess is sized to provide a nesting position for at least one of the first and second projections.

27. The method of claim 12 further comprising forming at least one undercut region in at least one of the abutments.

28. The method as set forth in claim 12 further comprising forming an outer edge on at least one of the abutments which is substantially parallel to an opposing surface on the one of the barrel and plunger with the plurality of interconnected slots.

29. The method as set forth in claim 12 further comprising forming a rear face on at least one of the abutments which has an arc shape.

30. The method as set forth in claim 11 further comprising forming the first and second projections to extend in at least partially opposing directions.

31. The plunger of claim 1, wherein the plunger rotates into a position engageable with said needle at the end of depression of the plunger to facilitate retraction of said needle.

32. The plunger of claim 31, wherein the plunger following engagement of said retractable needle by said plunger, said plunger and needle engaged therewith rotate into an inoperable position to prevent re-use of the syringe.

33. The plunger of claim 32, wherein said first projection and said second projection bear against respective abutments in respective slots of said plunger.

34. The syringe of claim 6 wherein the plunger rotates into a position engageable with said needle at the end of depression of the plunger to facilitate retraction of said needle.

35. The syringe of claim 34 wherein the plunger following engagement of said retractable needle by said plunger, said plunger and needle engaged therewith rotate into an inoperable position to prevent re-use of the syringe.

36. The syringe of claim 35, wherein said first projection and said second projection bear against respective abutments in respective slots of said plunger.

37. The method of claim 11 wherein the plunger rotates into a position engageable with said needle at the end of depression of the plunger to facilitate retraction of said needle.

38. The method of claim 37, wherein the plunger following engagement of said retractable needle by said plunger, said plunger and needle engaged therewith rotates into an inoperable position to prevent re-use of the syringe.

39. The method of claim 38, wherein said first projection and said second projection bear against respective abutments in respective slots of said plunger.

40. The plunger of claim 1, which is capable of rotating 180 degrees from when said first projection is initially located in said first slot and said second projection is initially located in said retraction slot to when said first projection is located within said retraction slot; and initially said second projection is located in said first slot.

41. The syringe of claim 6, which is capable of rotating 180 degrees from when said first projection is initially located in said first slot and said second projection is initially located in said retraction slot to when said first projection is located within said retraction slot; and initially said second projection is located in, said first slot.

* * * * *